United States Patent [19]

Can

[11] Patent Number: 4,707,318

[45] Date of Patent: Nov. 17, 1987

[54] METHOD FOR MANUFACTURING A SWAB

[76] Inventor: Tran D. Can, 23, Avenue Niel, 75017 Paris, France

[21] Appl. No.: 725,118

[22] Filed: Apr. 19, 1985

Related U.S. Application Data

[63] Continuation-in-part of Ser. No. 474,184, Mar. 10, 1983, abandoned.

[30] Foreign Application Priority Data

Mar. 12, 1982 [FR] France ................................ 82 04167
Aug. 13, 1982 [FR] France ................................ 82 14139

[51] Int. Cl.$^4$ .............................................. B29C 43/18
[52] U.S. Cl. ................................... 264/138; 264/250; 264/266; 264/293; 264/296; 264/320; 264/324
[58] Field of Search ............... 264/103, 266, 293, 296, 264/310, 320, 324, 250, 138; 604/1; 425/322, 363, 369, 385, 392

[56] References Cited

U.S. PATENT DOCUMENTS 2,987,063 6/1961 Glickston ............................ 128/269
4,547,253 10/1985 Heaney et al. .................. 264/293 X Primary Examiner—Jeffery Thurlow
Assistant Examiner—Leo B. Tentoni
Attorney, Agent, or Firm—Steinberg & Raskin

[57] ABSTRACT

A swab, such as for removing wax from the auditory meatus of an ear, includes a wad of absorbent material, such as cotton, arranged on an end of a stem and wherein the wad has a non-circular external configuration in a cross-section taken through a plane transverse to the axis of the stem. The wad may have at least one channel formed in the outer surface in which the material to be removed, i.e., the wax, becomes situated during the removal operation. The invention is particularly applicable to swabs which are intended for use by children or persons having delicate auditory meatus'. The stem of the swab is formed of deformable material and in manufacture the wad-stem assembly portion of the swab is subjected to a deformation pressure until the desired non-circular configuration of the wad is obtained. The wad supporting end of the stem is deformed at the same time to provide a non-circular configuration which substantially corresponds to the external cross-sectional configuration of the wad.

21 Claims, 20 Drawing Figures

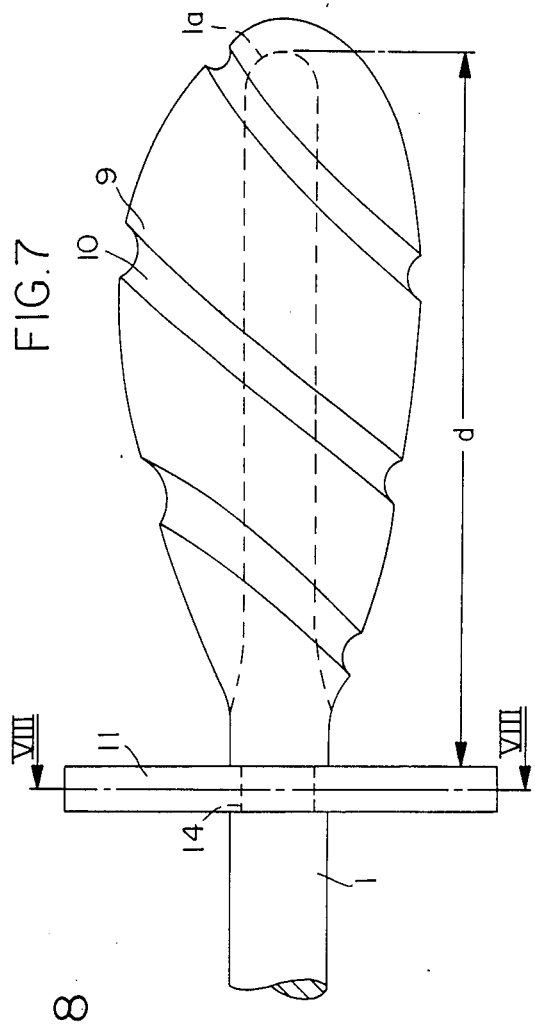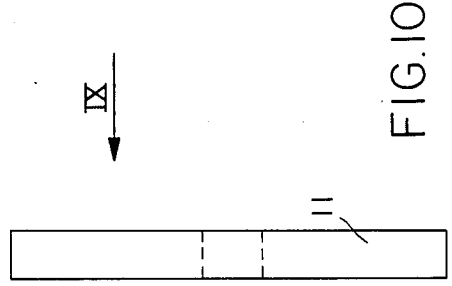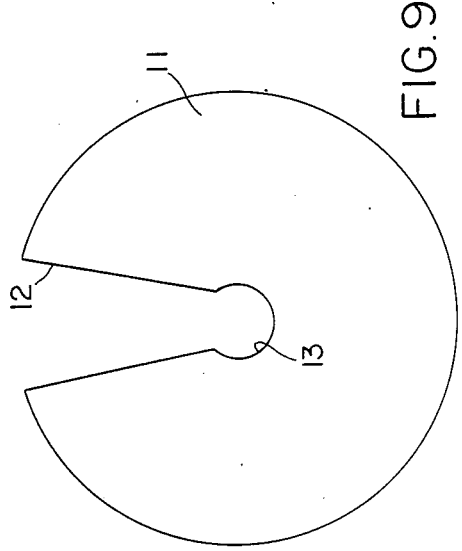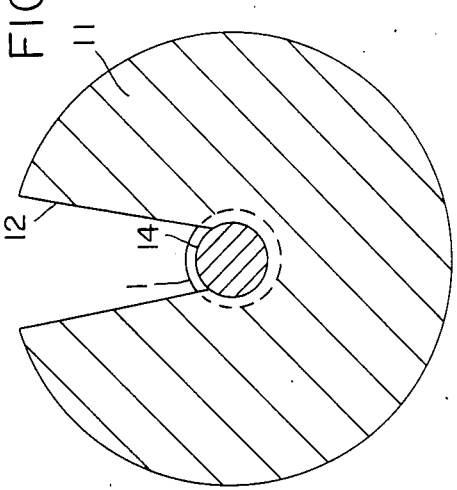

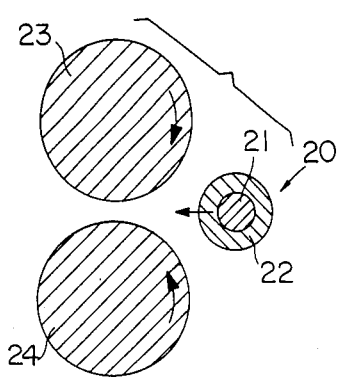
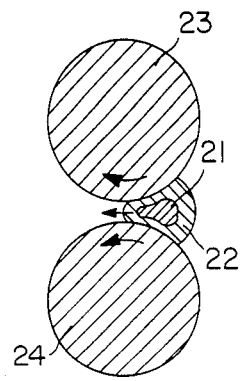
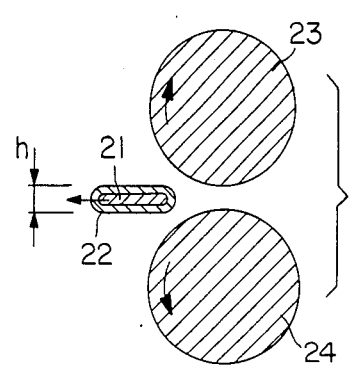
FIG.11   FIG.12   FIG.13
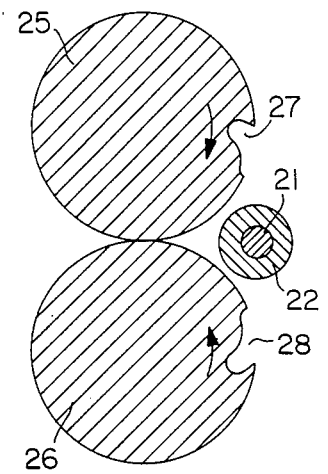
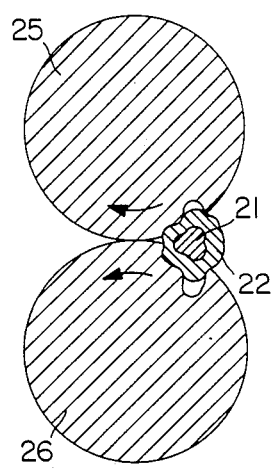
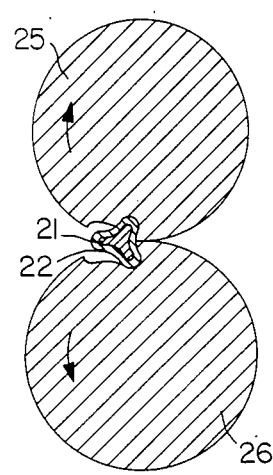
FIG.14   FIG.15   FIG.16
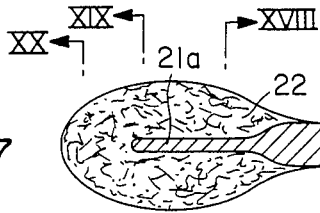
FIG.17
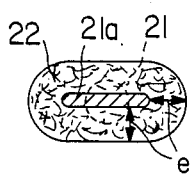
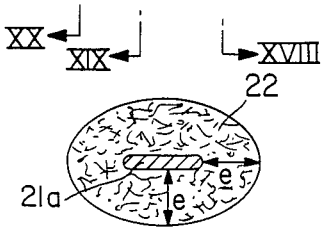
FIG.18   FIG.19   FIG.20

METHOD FOR MANUFACTURING A SWAB

BACKGROUND OF THE INVENTION

This application is a continuation-in-part of co-pending application Ser. No. 474,184 filed Mar. 10, 1983.

The present invention relates generally to articles of personal hygiene and, more particular, to swabs for removing material from tubular passages in the body, namely for removing wax from the auditory meatus of the ear and to methods for their manufacture. One type of such article is known as a "cotton swab".

The use of cotton swabs has expanded to a great extent in recent years. In fact, the use of such cotton swabs has essentially replaced the use of matches, hair pins or other articles around which persons would wind a small piece of cotton in order to clean the ear, in particular the auditory meatus of the ear.

However, conventional cotton swabs cannot always be advantageously employed, especially by a person having a relatively narrow or sensitive auditory meatus. In particular, the use of cotton swabs is generally not advised by pediatricians and doctors for the treatment of small children.

Thus, an improper utilization of a conventional cotton swab may actually force the ear wax further into the auditory meatus where it eventually forms a plug, the removal of which often requires hospital treatment. Obviously, the use of home made devices, such as a match having a cotton ball would around its tip, is subject to the same drawbacks. The use of other expedients, such as a piece of cotton dipped in an alcoholic solution without a rigid support, is also clearly not advisable.

SUMMARY OF THE INVENTION

It is an object of the present invention to provide new and improved swabs by which the above-mentioned drawbacks are eliminated.

Another object of the present invention is to provide new and improved methods for manufacturing a swab.

Briefly, in accordance with the present invention these and other objects are attained by providing in a swab including a stem on at least one end of which a wad of absorbent material, such as cotton, is situated, that the wad is formed having a noncircular external configuration in a cross-section taken through a plane transverse to the axis of the stem. In this manner, upon introduction of the wad into the auditory meatus, the ear wax will not be forced to any substantial extent further into the meatus, the ear wax collecting in spaces defined between the wad and the wall of the auditory meatus. In certain embodiments the spaces are defined by at least one channel formed in the outer surface of the wad so that the ear wax collects in the channels as the wad advances in the auditory meatus.

It will be readily understood that in the use of a swab according to the present invention, when the swab is introduced into the auditory meatus and rotated therein, the ear wax will collect in the spaces provided by the non-circular external cross-sectional configuration of the wad. The risk of compression of the ear wax by the wad is thereby considerably reduced and indeed substantially eliminated since after the wad is introduced into the meatus, it will only bear against the specific welldefined region of the wall of the auditory meatus.

Another feature of the present invention makes it possible to reliably prevent accidents during use of the swabs, especially when such swabs are used on very young children. In this connection, it is known that frequent cleaning of children's ears is necessary due to the abundant formation of ear wax. More particularly, only the visible parts of the ears of very young children, namely the pinna and external parts of the auditory meatus, should be cleaned. However, even a cleaning of these external parts may in some cases be dangerous due to the possible lack of cooperation of a struggling child as well as the possibility of contacting a reflex zone which may trigger an abrupt movement of the child. The possibility of such unexpected movements of the child during cleaning of the ear with a swab thus presents the risk of an inadvertent insertion of the swab fully into the external auditory meatus with the possible danger of perforating the tympanum by the relatively rigid stem that supports the cotton swab.

In accordance with the present invention, the risk described above is eliminated by providing a shield affixable to the stem of the swab so as to extend substantially perpendicular thereto. The shield is situated at a certain distance from the tip of the stem on which the wad is arranged, such distance being significantly smaller than the distance between the entrance of the auditory meatus and the tympanum of the ear to be cleaned by the swab. The shield is preferably affixed to a precisely predetermined location on the stem in a removable fashion, the shield and stem comprising cooperating closing and locking means.

It is a feature of the invention that the swab is constructed in a certain manner which will maintain the external non-circular cross-sectional configuration of the wad substantially permanently. The swab stem is formed of deformable material and during manufacture the wad-stem assembly portion of the swab is subjected to a deformation pressure until the desired configuration of the wad is obtained. At the same time the wad supporting end of the stem is deformed to have a non-circular configuration which substantially corresponds to the external cross-sectional configuration of the wad. In addition to serving to maintain the non-circular configuration of the wad, this construction facilitates and accelerates the manufacturing operation and improves the comfort and safety of the swab in use as described in greater detail below.

DESCRIPTION OF THE DRAWINGS

A more complete appreciation of the present invention and many of the attendant advantages thereof will be readily understood by reference to the following detailed description when considered in connection with the accompanying drawings in which:

FIG. 7 is a schematic elevation view of a swab according to the present invention provided with shield means for preventing inadvertent over-insertion of the swab into the auditory meatus;

FIG. 8 is a section view taken along line VIII—VIII of FIG. 7;

FIG. 9 is a side elevation view of shield means forming a component of the swab of the present invention, the shield means being shown separated from the swab and constituting a view in the direction of arrow IX of FIG. 10;

FIG. 10 is a side elevation view of the shield means illustrated in FIG. 9;

FIGS. 11, 12 and 13 are schematic sectional views illustrating a calendering deformation sequence for manufacturing a swab in accordance with the invention wherein, FIG. 11 shows a wad-stem assembly portion of a swab being manufactured prior to a deformation step and having an external circular cross-sectional configuration;

FIG. 12 shows the wad-stem assembly portion during the deformation step; and

FIG. 13 shows the finished wad-stem assembly portion after the deformation step and having an external non-circular crosssectional configuration;

FIGS. 14, 15 and 16 are schematic sectional views illustrating another embodiment of a calendering deformation sequence for manufacturing a swab in accordance with the invention wherein FIGS. 14, 15 and 16 show a wad-stem assembly portion of a swab prior, during and after a deformation step respectively in a manner corresponding to FIGS. 11, 12 and 13, FIG. 17 is a longitudinal section view of a wad-stem assembly portion manufactured in accordance with the calendering deformation sequence illustrated in FIGS. 11-13; and FIGS. 18, 19 and 20 are section views taken along lines XVIII—XVIII, XIX—XIX and XX—XX of FIG. 17 respectively.

DESCRIPTION OF THE PREFERRED EMBODIMENTS

Figure 1:
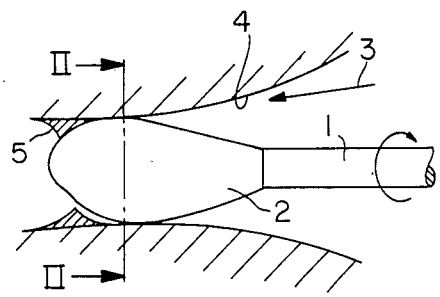
FIG. 1 is a schematic elevation view in section of a prior art swab shown as inserted into the auditory meatus and acting on ear wax situated therein.
Figure 2:
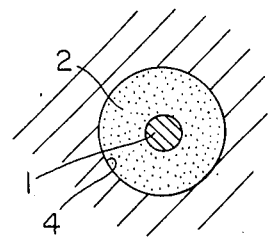
FIG. 2 is a section view taken along line II—II of FIG. 1.

Referring now to FIGS. 1-10 wherein like reference characters designate identical or corresponding parts throughout the several views, a conventional swab according to the prior art is illustrated in FIGS. 1 and 2. The conventional swab comprises a stem 1 around at least one end of which a wad formed of cotton or similar absorbent material is wound. When it is desired to clean the auditory meatus, the tip of the cotton swab carrying the wad 2 is introduced into the interior of the auditory meatus 4 in the direction of arrow 3.

It has been found, however, that the use of the above technique with conventional swabs will often push the ear wax 5 further into the auditory meatus, especially when the auditory meatus is very large, such as where young children are concerned. The ear wax which is pushed further into the auditory meatus has a tendency to accumulate at the bottom of that passage and form a plug-type obstruction which is difficult to remove.

FIGS. 1 and 2 clearly illustrates a typical example of the drawbacks mentioned above in connection with conventional swabs, it being noted that the section II—II of the wad 2 completely fills the auditory meatus 4 so that as the wad 2 advances, the wax 5 is prevented from collecting on the surface of the wad regardless of the rotation of stem 1 and that as the swab is advanced in the direction of arrow 3, the wax 5 is pushed further into the area of the auditory meatus.

According to the principle of one aspect of the present invention, an improved swab is obtained by providing the wad with a channel in which the ear wax will enter as the swab is inserted into the auditory meatus so that even in cases where the wad completely fills the passage, the wax will not be pushed in front of the wad but will pass through the channel to thereby allow it to collect on the wad surface.

Figure 3:
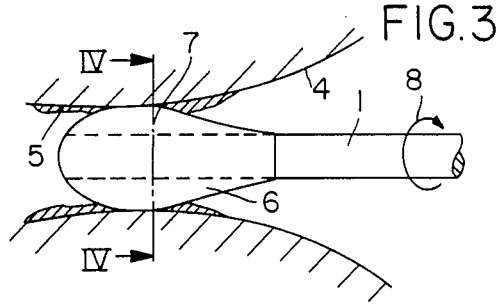
FIG. 3 is a schematic elevation view in section of one embodiment of a swab in accordance with the present invention shown as inserted into the auditory meatus and acting on ear wax situated therein.
Figure 4:
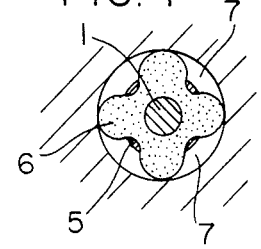
FIG. 4 is a section view taken along line IV—IV of FIG. 3.

According to the embodiment of the invention illustrated in FIGS. 3 and 4, the wad 6, preferably comprising a cotton wad, has a substantially oval outer configuration when viewed in a direction perpendicular to the axis of the stem end 1 designated by the dash-dot line of FIG. 3. This is similar to the outer configuration of the wad 2 of the prior art swab of FIGS. 1 and 2. However, the cross-section of the wad 6 in the plane substantially transverse to the axis of the stem is not circular as in the case of the prior art but, rather, has a cross-shaped configuration (FIG. 4) wherein four branches define between them four substantially longitudinally extending channels 7.

It will be readily understood by those skilled in the art that with this configuration of the wad, the ear wax will not be pushed towards the bottom of the meatus but will enter into the channels 7 as clearly seen in FIG. 4.

Additionally, it will also be understood that upon rotating the swab about the axis of the stem end 1 as designated by arrow 8 in FIG. 3, ear wax situated in the auditory meatus will gather in the interior of the channels 7.

Figure 5:
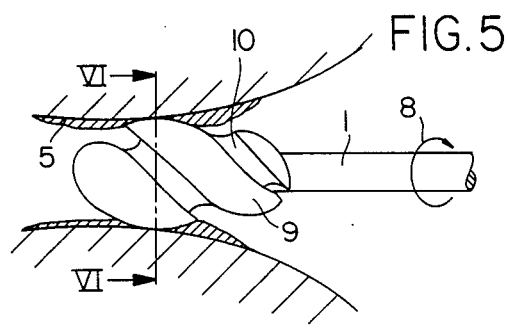
FIG. 5 is a schematic elevation view in section of another embodiment of a swab according to the present invention shown as inserted into the auditory meatus and acting on ear wax situated therein.
Figure 6:
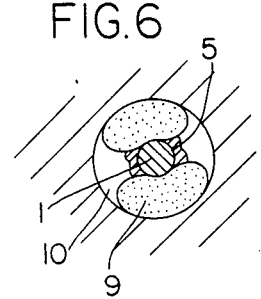
FIG. 6 is a section view taken along line VI—VI of FIG. 5.

In the embodiment of the invention illustrated in FIGS. 5 and 6, the wad 9 formed of cotton and having substantially the same outer configuration as wads 2 and 6 is formed with a channel 10 which follows a substantially helical path. The ear wax 5 will enter into and accumulate within the channel 10 in a manner similar to that described above in connection with FIGS. 3 and 4 so that there will be little tendency for the ear wax to be compressed at the bottom of the auditory meatus. The helical configuration of the channel has the additional advantage that upon rotation of the swab in the direction by arrow 8 in FIG. 5, the ear wax will tend to be withdrawn from the meatus.

It is to be understood that the invention is not limited to the particular details of the illustrated embodiments. For example, the channels 7 of the embodiment of FIGS. 3 and 4 can twist around the longitudinal axis or even be substantially helical rather than substantially longitudinal as shown. This alternate construction indeed may improve the efficiency of the swab. Moreover, several parallel helical channels 10 can be formed on the wad 9 in the embodiment of FIGS. 5 and 6.

In order to form a wad of the type illustrated in FIGS. 3-6 so as to have a configuration in accordance with the present invention, several procedures are possible. In a first embodiment of the method, a cotton wad is first formed to have the general oval shape of the conventional wad 2 shown in FIGS. 1 and 2. The wad is then compressed, preferably under heat, in an appropriate mold to provide the desired configuration.

Thus, the appropriate configuration can be obtained by subjecting a conventional cotton wad to pressure, preferably accompanied by heat. Such a technique can be carried out in a quick, easy and economical manner.

If it is desired to provide a firmer form of the cotton wad so that the channels will remain well defined over long periods of time, in addition to other advantages, the wad can be coated with an appropriate stiffener, such as starch.

Other manufacturing techniques can be used. For example, in order to form a cotton wad of the type illustrated in FIGS. 5 and 6, cotton can be wrapped around the end of the stem in the form of a helix. A glue or adhesive can be applied over the end of the stem in order to facilitate the wrapping as well as in order to enhance the firmness of the cotton wad.

Other materials than cotton may be utilized to form the wad. For example, synthetic foam materials are known which are readily formable under heat to have the cross-sectional shapes in accordance with the present invention. Of course, it is understood that the material must be non-allergic and have appropriate softness.

According to another aspect of the invention, the swab can be constructed in a manner which facilitates shaping of the wad to have an external non-circular cross-sectional configuration and which, moreover, improves its behavior and safety in use as well as the comfort of the user.

In particular, the stem which supports the wad at its end is made of a material which deforms under pressure. During manufacture, one of the ends of the stem is fitted with a cotton wad or the like to form a wad-stem assembly portion of the swab. At this stage of manufacture, the external cross-sectional configuration of the wad can have any form, such as circular. The wad-stem assembly portion is subjected to a pressure deformation step whereupon the external cross-sectional configuration of the wad is given the desired non-circular configuration. At the same time the wad supporting end of the stem is deformed to provide a non-circular configuration which substantially corresponds to the external cross-sectional configuration of the wad.

The stem is preferably formed of a thermoplastic material and the pressure deformation step is then preferably applied under heated conditions to provide the stem with a permanent deformation. The pressure deformation step is most advantageously carried out by passing the wad-stem assembly portion of the swab between a pair of calender rolls which are heated to a temperature sufficiently high to insure permanent deformation of the stem.

This technique results in the external non-circular cross-sectional configuration of the wad being maintained substantially permanently in that the end portion of the stem which supports the wad is itself deformed under the layer of the cotton wad and cooperates therewith to maintain the non-circular cross-sectional external configuration.

Furthermore, the technique described above can be accomplished so that the thickness of the cotton wad is substantially constant over the perimeter of the supporting stem portion in any plane which passes through the wad-stem assembly portion transversely to the stem. This feature insures that the swab can be used in a comfortable and safe manner compared to a situation where the thickness of the cotton layer wrapped around the stem might have thin portions or situations where the surface of the stem is exposed thereby raising the possibility that the supporting stem may directly contact the wall of the auditory meatus. Still further, the technique described above also considerably facilitates and accelerates the manufacturing operation.

Referring now to FIGS. 11-20 wherein like reference characters designate identical or corresponding parts throughout the several views, and more particularly to FIGS. 11-13, a transverse crosssectional view of a wad-stem assembly portion of a swab is designated 20 in FIG. 11. The wad-stem assembly portion 20 shown in FIG. 11 comprises a cotton wad 22 wrapped around the supporting end of a stem 21 formed of thermoplastic material. The wad-stem assembly portion 20 of the swab is shown in FIG. 11 prior to a deformation step and the stem 21 has a substantially circular external cross-sectional configuration as does the cotton wad 22. Indeed, the cross-sectional configuration of the wadstem assembly portion shown in FIG. 11 is substantially the same as that of conventional swabs. It will be understood that although the wad 22 is described herein as being made of cotton, other suitable material formed of natural or synthetic physiologically compatible wadding material can be used.

The wad-stem assembly portion 20 is subjected to a pressure deformation step to provide the wad with a desired external non-circular cross-sectional configuration. In accordance with the embodiments shown in FIGS. 11-13, the initially circular wad-stem assembly portion is pressed between a pair of spaced calendering rolls 23, 24 rotating in the directions designated by the arrows. FIG. 12 shows the wad-stem assembly portion during the pressure deformation step as it is compressed between the calendering rolls and the finished wad-stem assembly portion is shown in FIG. 13 as having an external flattened cross-sectional configuration. It is noted in FIG. 13 that the wad supporting ends of the stem 21 is deformed to have a non-circular configuration which substantially corresponds to the external cross-sectional configuration of the wad 22 which functions to maintain the external non-circular cross-sectional configuration of the wad substantially permanently.

As noted above, the support stem 21 is preferably made of a heat deformable plastic compound, i.e. a thermoplastic compound, and the calendering rolls 23, 24 are preferably heated to a suitable temperature during the manufacturing operation. Thus, the rolls are preferably heated to a temperature such that the stem 21 will be heated to a temperature close to the softening point of the thermoplastic material of which it is formed. In practice, since the calendering rolls are generally run at a relatively high speed, the rolls will be heated to a temperature higher than the softening point of the material from which the stem 21 is formed to permit the stem to be sufficiently heated even though the time spent by the wad-stem assembly portion between the rolls is relatively short. A person skilled in the art can readily select a particular temperature at which the calendering rolls are operated in view of the rotational speed of the rolls, the material from which the stem 21 is formed and the grade of cotton wad 22 which is used.

It will also be understood that the final thickness h of the wad-stem assembly portion can be varied as desired by appropriately varying the space in between the calendering rolls 23 and 24.

It is also possible to obtain different external crosssectional configurations of the wad by appropriately varying the shape of the calender rolls. In this connection reference is made to FIGS. 14-16. In this embodiment the cylindrical surfaces of the calendering rolls 25 and 26 are generally in nip-defining relationship with each other. Each of the calendering rolls 25 and 26 are provided with a forming recess or cavity 27 and 28 shaped to provide the wad-stem assembly portion with a particular desired external configuration. As the calendering rolls rotate, the cavities 27 and 28 move into opposed relationship whereupon the wad-stem assembly portion is received in the cooperating cavities and subjected to a pressure deformation to obtain the desired non-circular external cross-sectional configuration. In the illustrated embodiment, the finished swab head has a three arm cross-shaped cross-sectional configuration, although it is understood that any non-circular configuration can be obtained through the provision of suitably formed cavities in the calendering rolls. It is also noted that during the pressure deformation step, at the same time as the wad 22 is deformed, the wad supporting end of the stem 22 is deformed to have a non-circular configuration which substantially corresponds to the external cross-sectional configuration of the wad.

Referring now to FIGS. 17-20, detailed views of the flattened wad-stem assembly portion produced by the calendering deformation sequence shown in FIGS. 11-13 are illustrated.

As seen in FIGS. 17 and 18, the wad supporting end 21a of the stem 21 is flattened during the pressure deformation step and is surrounded or wrapped over its entire periphery with a cotton layer having a substantially constant thickness e. By this feature, the swab provides maximum comfort and safety during use substantially eliminating any risk of direct contact between the stem and the auditory meatus.

Referring now to the embodiment of the invention illustrated in FIGS. 7-10, a swab is shown including a wad 9 having a helical channel 10 positioned on the end of a stem 1, similar to the embodiment of FIGS. 5 and 6. As noted above, this configuration facilitates the cleaning operation of the ears while preventing the compression of ear wax towards the bottom of the auditory meatus.

In accordance with a further aspect of the present invention, a shield 11 is affixed proximate to the end of the wad 9. In the illustrated embodiment, the shield 11 has a substantially flat or planar, circular configuration. An inwardly tapering slot 12 extends from the periphery of the shield 11 and terminates at a central opening 13, the diameter of which substantially corresponds to the diameter of an annular groove 14 formed in the stem 1. The annular groove 14 is formed at a distance d from the free tip end 1a of the stem 1. The distance d is generally chosen so as to be substantially smaller than the distance between the entrance to the auditory meatus and the tympanum of the ear in which the swab is to be inserted. This provision is especially advantageous in the case of young children from 2 to 5 years old. Indeed, a relatively great margin of safety should be provided where it is not necessary to clean the auditory meatus completely. In this case, the distance d is shorter.

It will be understood that the shield 11 is affixed to the swab by passing the stem 1 through the slot 12 until the edges of opening 13 of the shield are received in the groove 14 of the stem 1. The flanges defining the groove 14 prevent any axial movement of the shield 11 over the stem 1.

The shield 11 prevents the penetration of the stem 1 beyond the distance d even in the case of the child making an abrupt movement while the swab is inserted in the ear. The shield 11 is advantageously constructed of a transparent or translucent, i.e., a light-transmitting material, preferably being relatively soft.

The shield 11 can be easily removed from the stem 1 by merely urging the stem 1 out from opening 13. The advantage of providing a shield which is removable in this fashion is that a single shield is sufficient for an entire box of cotton swabs. Additionally, a separated shield does not present any problem in connection with the storing or packing of the article.

It will be understood that other ways of fixing and positioning the shield are possible within the scope of the present invention. Additionally, two or more grooves 14 may be provided along the length of the stem 1, the appropriate groove for receiving the shield being chosen in consideration of the age of the child into whose ear the swab will be inserted.

Obviously, numerous modification and variations of the present invention are possible in the light of the above teachings. It is therefore to be understood that within the scope of the claims appended hereto, the invention may be practiced otherwise than as specifically disclosed herein.

What is claimed is:

1. A method of making swabs including an elongate stem having ends and at least one wad of absorbent material supported on a respective end of the stem, comprising the steps of:
    forming the stem of a deformable material;
    providing the wad of absorbent material on a respective end of the stem to form a wad-stem assembly portion; and
    subjecting the wad-stem assembly portion to a pressure deformation to impart an external non-circular transverse cross-sectional configuration to both the wad and said respective end of the stem.

2. The method of claim 1 wherein the stem is formed of a thermoplastic material and the pressure deformation step carried out under heat.

3. The method of claim 1 where in the pressure deformation step is carried out between calender rolls.

4. The method of claim 3 wherein the calender rolls are spaced from each other.

5. The method of claim 3 wherein the calender rolls have corresponding recesses formed in respective surfaces thereof.

6. The method of claim 3 wherein the stem is formed of a thermoplastic material and the calender rolls are heated during the pressure deformation step.

7. The method of claim 1 wherein the non-circular transverse cross-sectional configuration of the end of the stem substantially corresponds to the non-circular cross-sectional external configuration of the wad.

8. Method of claim 7 wherein after the pressure deformation step, the thickness of the wad in a transverse cross-sectional plane through the wad-stem assembly portion is substantially constant.

9. The method of claim 1, comprising the additional step of
    attaching a shield to said stem at a distance from an end of said stem on which said wad is situated, for preventing said wad from being inserted in a tubular passage, such as an auditory meatus of an ear, beyond a predetermined point.

10. The method of claim 9, wherein said shield attaching step additionally comprises
    orienting said shield substantially perpendicularly to an axis of said stem.

11. The method of claim 9, comprising the additional steps of
forming a slot in said shield to extend from a periphery thereof and terminate at an opening in a central region of said shield, and
forming an annular groove in said stem,
whereby said shield is removably attached to said stem.

12. The method of claim 5, comprising the additional step of
rotating said calendar rolls in opposite directions.

13. The method of claim 1, comprising the additional step of
forming said wad to have a substantially oval configuration in a direction peripendicular to an axis of the stem end.

14. The method of claim 1, comprising the additional step of
overlying the entire surface of said stem end with said wad to form said wad-assembly portion,
whereby no region of said stem end is externally exposed.

15. The method of claim 1, comprising the additional step of
forming at least one channel in said wad so that when said swab is used to clean a passage such as an auditory meatus of an ear, said wad is introduced into the auditory meatus without forcing ear wax further thereinto, and with the ear wax entering the at least one channel formed in the wad.

16. The method of claim 15, wherein the channel is formed to follow a substantially helical path.

17. The method of claim 15, wherein four longitudinally extending channels are formed in the wad.

18. The method of claim 15, wherein the channel is formed only in the wad and does not extend into the stem.

19. The method of claim 3, comprising the additional step of
rotating said calendar rolls in opposite directions.

20. The method of claim 19, wherein the swab is passed between the calendar rolls in a direction substantially parallel to the cross-section thereof.

21. The method of claim 7, wherein the wab-stem assembly portion is formed to have three arm cross-shaped cross-sectional configuration.

* * * * *